(12) United States Patent
Sarkinen et al.

(10) Patent No.: US 8,657,587 B2
(45) Date of Patent: Feb. 25, 2014

(54) END OF STROKE DETECTION FOR ELECTROMAGNETIC PUMP

(75) Inventors: Scott A. Sarkinen, Greenfield, MN (US); James M. Haase, Maplewood, MN (US); Ronald L. Mezera, Lake Elmo, MN (US); Christian Michel Peclat, Neuchatel (CH)

(73) Assignee: Medtronic, Inc., Minneapolis, MN (US)

( * ) Notice: Subject to any disclaimer, the term of this patent is extended or adjusted under 35 U.S.C. 154(b) by 46 days.

(21) Appl. No.: 13/190,769

(22) Filed: Jul. 26, 2011

(65) Prior Publication Data

US 2011/0280737 A1    Nov. 17, 2011

Related U.S. Application Data

(63) Continuation of application No. 11/805,124, filed on May 22, 2007, now Pat. No. 8,007,247.

(51) Int. Cl.
*F04B 49/06* (2006.01)
*F04B 35/04* (2006.01)

(52) U.S. Cl.
USPC .................. 417/44.11; 417/44.1; 417/415

(58) Field of Classification Search
USPC ............ 417/44.1, 44.11; 324/207.11, 207.16, 324/207.14
See application file for complete search history.

(56) References Cited

U.S. PATENT DOCUMENTS

| | | | |
|---|---|---|---|
| 3,744,243 A | 7/1973 | Faisandier | |
| 4,487,603 A * | 12/1984 | Harris | 604/152 |
| 4,568,250 A | 2/1986 | Falk et al. | |
| 4,569,641 A | 2/1986 | Falk et al. | |
| 4,594,058 A | 6/1986 | Fischell | |
| 4,636,150 A | 1/1987 | Falk et al. | |
| 4,684,368 A | 8/1987 | Kenyon | |
| 4,714,234 A | 12/1987 | Falk et al. | |
| 4,717,874 A * | 1/1988 | Ichikawa et al. | 324/207.16 |
| 4,772,838 A | 9/1988 | Maresca | |
| 4,851,959 A * | 7/1989 | Stumpf | 361/159 |
| 4,950,985 A * | 8/1990 | Voss et al. | 324/207.16 |
| 4,985,015 A | 1/1991 | Obermann et al. | |
| 5,172,298 A * | 12/1992 | Shimizu et al. | 361/152 |
| 5,318,521 A | 6/1994 | Slettenmark | |
| 5,342,176 A * | 8/1994 | Redlich | 417/212 |
| 5,462,525 A | 10/1995 | Srisathapat et al. | |

(Continued)

FOREIGN PATENT DOCUMENTS

| WO | WO 03/023226 A1 | 3/2003 |
|---|---|---|
| WO | WO 2005/097235 A2 | 10/2005 |
| WO | WO 2005/097235 A3 | 1/2006 |

OTHER PUBLICATIONS

International Search Report and Written Opinion for PCT/US2008/061142; 12 pgs.

(Continued)

*Primary Examiner* — Charles Freay
*Assistant Examiner* — Alexander Comley

(57) ABSTRACT

Detection of end of stroke for an electromagnetic pump may be performed using, for example, a calculated first flux derivative. Further, inductance of a coil that can be energized to produce a pump stroke may be calculated (e.g., the pump may include an actuator moveable in response to the energization of the coil). For example, the inductance may be calculated as a function of sense coil current and source electrical potential when the actuator is not moving for use in determining position of the actuator.

15 Claims, 8 Drawing Sheets

(56) References Cited

U.S. PATENT DOCUMENTS

| | | | |
|---|---|---|---|
| 5,578,904 A * | 11/1996 | Marcott et al. | 324/207.16 |
| 5,583,434 A * | 12/1996 | Moyers et al. | 324/207.16 |
| 5,600,237 A * | 2/1997 | Nippert | 324/207.16 |
| 5,804,962 A * | 9/1998 | Kather et al. | 324/207.16 |
| 5,809,157 A | 9/1998 | Grumazescu | |
| 5,841,621 A * | 11/1998 | Dean et al. | 361/185 |
| 5,942,892 A * | 8/1999 | Li | 324/207.16 |
| 6,099,495 A * | 8/2000 | Kinghorn et al. | 604/93.01 |
| 6,280,148 B1 | 8/2001 | Zengerle et al. | |
| 6,577,133 B1 * | 6/2003 | Barron | 324/415 |
| 6,595,756 B2 * | 7/2003 | Gray et al. | 417/44.1 |
| 6,623,246 B2 | 9/2003 | Hwang et al. | |
| 6,652,510 B2 | 11/2003 | Lord et al. | |
| 6,663,348 B2 | 12/2003 | Schwarz et al. | |
| 6,724,606 B2 * | 4/2004 | Seale et al. | 361/160 |
| 6,805,693 B2 | 10/2004 | Gray et al. | |
| 6,895,997 B2 * | 5/2005 | Qu et al. | 137/554 |
| 6,942,469 B2 | 9/2005 | Seale et al. | |
| 6,997,921 B2 | 2/2006 | Gray et al. | |
| 7,030,519 B2 | 4/2006 | Slettenmark | |
| 7,090,470 B2 | 8/2006 | Kim | |
| 7,186,236 B2 | 3/2007 | Gibson et al. | |
| 7,248,006 B2 | 7/2007 | Bailey et al. | |
| 7,255,690 B2 | 8/2007 | Gray et al. | |
| 7,271,563 B2 * | 9/2007 | Yoo et al. | 318/632 |
| 7,285,878 B2 | 10/2007 | McGill et al. | |
| 7,372,255 B2 | 5/2008 | Holliday | |
| 7,927,326 B2 | 4/2011 | Sarkinen et al. | |
| 8,007,247 B2 | 8/2011 | Sarkinen et al. | |
| 2003/0099550 A1 * | 5/2003 | Kim | 417/44.11 |
| 2004/0097782 A1 | 5/2004 | Korakianitis et al. | |
| 2004/0127852 A1 | 7/2004 | Gray et al. | |
| 2005/0168179 A1 | 8/2005 | McGill et al. | |
| 2006/0239842 A1 | 10/2006 | Yaguchi | |
| 2008/0269724 A1 | 10/2008 | Sarkinen et al. | |

OTHER PUBLICATIONS

International Preliminary Report on Patentability and Written Opinion for PCT/US2008/061142; 7 pgs.

* cited by examiner

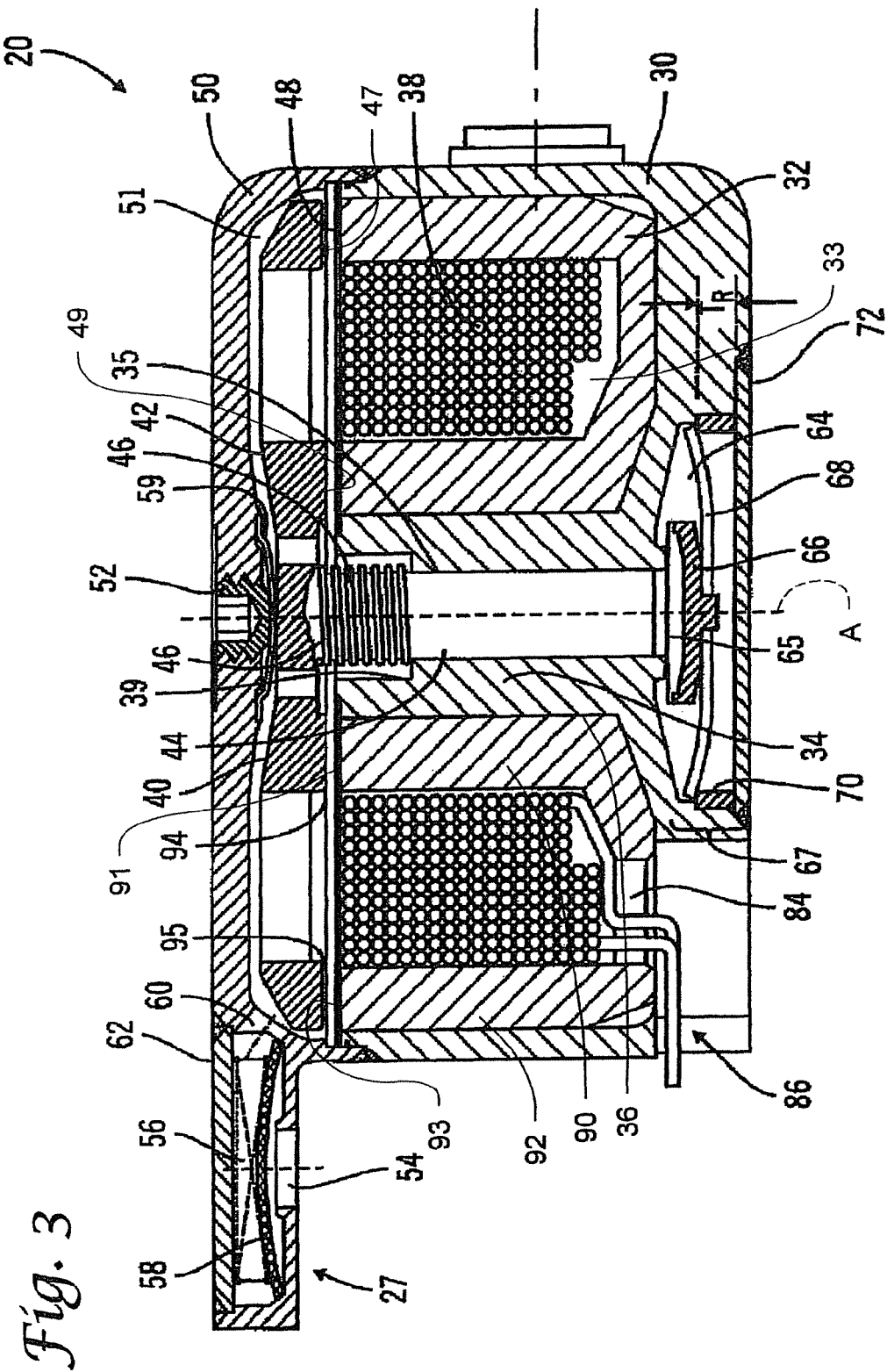

END OF STROKE DETECTION FOR ELECTROMAGNETIC PUMP

This is a continuation of application Ser. No. 11/805,124, filed May 22, 2007, which is incorporated herein by reference in its entirety.

TECHNICAL FIELD

The present invention relates generally to electromagnetic pumps (e.g., such as those used in infusion devices that are implantable or otherwise connected to patients), as well as to methods relating to such electromagnetic pumps.

BACKGROUND OF THE INVENTION

Infusion devices are typically used to deliver an infusion medium, such as a medication, to a patient. Implantable infusion devices are designed to be implanted in a patient's body to administer an infusion medium to the patient at a regulated dosage, over a period of time. External infusion devices may be designed to be portable, for example, to be worn outside of the patient's body and connected to the patient by a catheter. Other fauns of infusion devices are non-portable devices, typically for use in a controlled environment, such as a hospital.

Electromagnetic pump mechanisms (e.g., mechanisms that include a coil and an actuator which moves relative thereto) are used in infusion devices to selectively drive infusion medium, for example, to a patient. Various forms of electromagnetic pumps have been developed for use in infusion devices operating in external or implant environments. For example, one or more various electromagnetic pump mechanisms are described in U.S. Pat. No. 4,594,058 issued 10 Jun. 1986 to Fischell, entitled "Single valve diaphragm pump with decreased sensitivity to ambient conditions"; U.S. Pat. No. 4,684,368 issued 4 Aug. 1987 to Kenyon, entitled "Inverted pump"; U.S. Pat. No. 4,569,641 issued 11 Feb. 1986 to Falk et al., entitled "Low power electromagnetic pump"; U.S. Pat. No. 4,568,250 issued 4 Feb. 1986 to Falk et al., entitled "Low power electromagnetic pump"; U.S. Pat. No. 4,636,150 issued 13 Jan. 1987 to Falk et al., entitled "Low power electromagnetic pump"; U.S. Pat. No. 4,714,234 issued 22 Dec. 1987 to Falk et al., entitled "Low power electromagnetic valve"; U.S. Pat. No. 6,595,756 B2 issued 22 Jul. 2003 to Gray et al., entitled "Electronic control system and process for electromagnetic pump"; U.S. Pat. No. 6,997,921 B2 issued 14 Feb. 2006 to Gray et al., entitled "Infusion device and driving mechanism for same"; U.S. Pat. No. 7,186,236 B2 issued 6 Mar. 2007 to Gibson et al., entitled "Infusion device and inlet structure for same"; U.S. Pat. No. 6,805,693 B2 issued 19 Oct. 2004 to Gray et al., entitled "Infusion device and driving mechanism for same"; and U.S. Pat. No. 6,652,510 B2 issued 25 Nov. 2003 to Lord et al., entitled "Implantable infusion device and reservoir for same."

Typically, electromagnetic pump configurations, such as those described in the above-referenced patents, employ a conductive coil of the pump coupled to a power source using control electronics. The coil is selectively energized by the power source and control electronics (e.g., using a controller and a switch) to create an electromagnetic field which operates on a moveable actuator (e.g., armature and piston). When the coil is energized, the electromagnetic field causes the actuator to move, for example, against the force of a spring, toward a stroke position. When the coil is then de-energized, the spring force, for example, returns the actuator to the position it had prior to energizing the coil. By moving the actuator between the energized stroke position and its return position, a pumping action is accomplished by the electromagnetic pump.

In many circumstances, such as when electromagnetic pumps are used in infusion devices, the electromagnetic pumps may be operable for extended periods of time with a limited power supply. For example, battery-powered infusion devices may be implanted in or otherwise connected to patients to deliver medication at controlled intervals over a prolonged period of time. As battery power supplies have limited capacities, such devices may require multiple replacements of batteries over their operational life. In the case of an electromagnetic pump used in an implanted infusion device, a replacement of a battery may require the surgical removal of the infusion device. Even with external devices, the replacement of a battery may require specialized tools, parts, or skills which necessitate the services of a specialist or trained technician. As such, in the art of electromagnetic pumps, for example, that are used in infusion devices, there is a desire to make efficient use of the power supply.

In many prior infusion devices, capacitor discharge power control circuits are used as the power source for the electromagnetic pump. Generally, such power control circuits include a capacitor that is charged by a battery and selectively discharged to the coil of the electromagnetic pump to power the pump operation. For example, each discharge of the capacitor delivers an electrical power pulse to the coil sufficient to energize the coil and cause the pump to make one complete stroke. The capacitor is charged by the battery between pump strokes.

To operate the electromagnetic pump under generally all expected power load conditions, the capacitor size of the power control circuits is generally selected such that the power output per complete discharge is sufficient to operate the pump in the greatest expected power load condition. As a result, sufficient power to operate the pump in the greatest expected load condition is provided to the pump, even when the pump is not operating under the greatest expected load. Such a complete power discharge at every pump stroke, independent of the pump's power needs, results in a waste of electrical power.

Various manners of attempting to decrease power consumption have been attempted. For example, generally, control signal circuitry is programmed or configured to generate a signal to control the closure of a switch coupling the power source to the electromagnetic pump upon the occurrence of one or more various events. For example, such events may include the expiration of a predetermined time period after initiation of a stroke and prior to initiation of a subsequent stroke. However, even prior to the expiration of a predetermined time period, end of stroke of the electromagnetic pump generally occurs. Allowing discharge of the capacitor (e.g., application of power to the electromagnetic pump) through expiration of the predetermined time period even when end of stroke has occurred would be an expenditure of unnecessary power.

As such, various techniques have been described for use in controlling the capacitor discharge to the electromagnetic pump to reduce power consumption. For example, in U.S. Pat. No. 6,595,756 to Gray et al., a detector for detecting the end of a pump stroke is described such that a power control circuit may cut off power to the pump coil prior to the detected end of the pump stroke. As described therein, for example, the back electromotive force (back EMF) of the coil is detected to determine when or where the actuator is capable of completing its full stroke motion after the capacitor discharge is cut off. By detecting or monitoring the back EMF generated in the coil, a suitable cut off time may be determined. Further, as described therein, a sharp positive rise or a change in direction of a coil current can indicate actuator deceleration that occurs at the actual end of the actuator's forward stroke. A suitable capacitor cut off point can also be selected based thereon.

SUMMARY OF THE INVENTION

The present invention provides for one or more methods of detecting the end of stroke for an electromagnetic pump. Using such information, power applied to the electromagnetic pump may be selectively cut to reduce energy consumption. For example, in one or more embodiments, the present invention uses both the coil potential and the coil current, as well as mathematical relationships between them, and the changing inductance, to provide reliable detection of end of stroke and also provide stroke position information for the electromagnetic pump (e.g., actuator position information which can be used as diagnostic information for the pump).

An electromagnetic pump system (e.g., such as a pump that is part of an implantable medical device) according to one embodiment of the present invention includes an electromagnetic pump. The pump includes a coil that can be energized to produce a pump stroke, wherein the electromagnetic pump further includes an actuator moveable in response to the energization of the coil. A power source is connected to selectively energize the coil of the electromagnetic pump, wherein the power source applies a source electrical potential to the coil to pass a coil current therethrough. A voltage sense device senses the source electrical potential applied to the coil and a current sense device senses the coil current. Further, the system includes control electronics to detect the end of a pump stroke based on a change in flux over time calculated as a function of sensed coil current and source electrical potential.

In one embodiment of the system, the control electronics calculates $U_{source}-(R_{coil}*I_{coil})$ over time corresponding to the change of flux over time, where $U_{source}$ is source electrical potential, $R_{coil}$ is the resistance of the coil, and $I_{coil}$ is the coil current. Further, in another embodiment, the control electronics performs peak detection to detect a peak in $U_{source}-(R_{coil}*I_{coil})$ as calculated over time corresponding to the end of a pump stroke.

An implantable infusion device for delivery of infusion medium according to one embodiment of the present invention includes a drive mechanism. The drive mechanism includes a coil that can be energized to produce a pump stroke, wherein the drive mechanism further includes an actuator moveable relative to the coil in response to the energization of the coil to deliver infusion medium. A power source is connected to selectively energize the coil of the electromagnetic pump, wherein the power source applies a source electrical potential to the coil to pass a coil current therethrough. One or more sense devices sense the source electrical potential applied to the coil and the coil current. Control electronics of the device detects the end of a pump stroke based on a change in flux over time calculated as a function of sensed coil current and source electrical potential. The control electronics includes a switch device connected between the power source and the coil to connect the power source to the coil at the initiation of a pump stroke and disconnect the power source from the coil upon detection of an end of the pump stroke.

Another embodiment of an electromagnetic pump system according to the present invention includes an electromagnetic pump. The pump includes a coil that can be energized to produce a pump stroke, wherein the electromagnetic pump further includes an actuator moveable in response to the energization of the coil. A power source is connected to selectively energize the coil of the electromagnetic pump, wherein the power source applies a source electrical potential to the coil to pass a coil current therethrough. A voltage sense device senses the source electrical potential applied to the coil and a current sense device for sensing the coil current. Control electronics calculates inductance of the coil as a function of sensed coil current and source electrical potential when the actuator is not moving for use in determining position of the actuator.

In one embodiment of the system, the control electronics calculates $(U_{source}-(R_{coil}+R_{source})*I_{coil})/d/dt\ I_{coil}$ for use in determining position of the actuator.

A method for use in controlling an electromagnetic pump (e.g., an electromagnetic pump that includes a coil that can be energized by a power source to produce a pump stroke and an actuator moveable in response to the energization of the coil) according to one embodiment of the present invention includes applying a source electrical potential to the coil to pass a coil current therethrough to provide a pump stroke. The source electrical potential applied to the coil and the coil current is sensed. The method further includes detecting the end of the pump stroke based on a change in flux over time calculated as a function of sensed coil current and source electrical potential.

In one embodiment, selectively applying a source electrical potential to the coil includes connecting the power source to the coil at the initiation of a pump stroke and disconnecting the power source from the coil upon detection of an end of the pump stroke. Further, the pump stroke may deliver infusion medium.

In another method for use in controlling an electromagnetic pump (e.g., an electromagnetic pump that includes a coil that can be energized by a power source to produce a pump stroke and an actuator moveable in response to the energization of the coil) includes applying a source electrical potential to the coil to pass a coil current therethrough to provide a pump stroke, sensing the source electrical potential applied to the coil, and sensing the coil current. Further, the method includes calculating inductance of the coil as a function of sensed coil current and source electrical potential for use in determining position of the actuator.

Yet further, back EMF may also be calculated as a function of sensed electrical potential and coil current for use in detecting end of pump stroke. Such calculated back EMF may be used alone to detect end of pump stroke or may be used to verify an already detected end of stroke.

The above summary is not intended to describe each embodiment of every implementation of the present invention. Rather, a more complete understanding of the invention will become apparent and appreciated by reference to the following detailed description and claims in view of the accompanying figures of the drawing.

BRIEF DESCRIPTION OF THE DRAWING

The present invention will be further described with reference to the figures of the drawing, wherein:

FIG. 3 is a cross-section view of one exemplary embodiment of the electromagnetic pump of FIG. 2, in a retracted position or state.

DETAILED DESCRIPTION OF EXEMPLARY EMBODIMENTS

Figure 2:
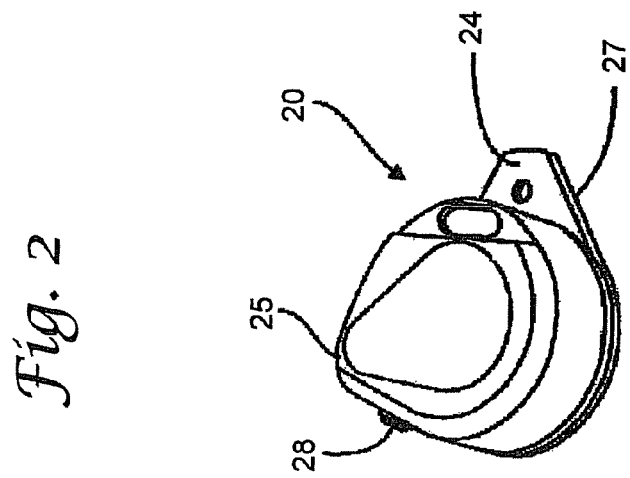
FIG. 2 is a perspective view of a drive mechanism or electromagnetic pump for an implantable infusion device according to one embodiment of the present invention.

In the following detailed description of the illustrative embodiments of the invention, references are made to the accompanying figures of the drawing which form a part hereof, and in which are shown, by way of illustration, specific embodiments in which the invention may be practiced. It is to be understood that other embodiments may be utilized and structural changes may be made without departing from the scope of the present invention.

As described herein, the present invention relates generally to electronic control systems, configurations, and processes for electromagnetic pumps. Embodiments of the present invention relate to such systems, configurations, and processes for efficient utilization of power and reduction of electrical power consumption requirements in electromagnetic pumps, particularly as they relate to the detection of an end of pump stroke, as well as employing such detection for the control of electromagnetic pumps. Yet further, other embodiments relate to the use of other calculated information for determining various characteristics of an electromagnetic pump, such as the position of an actuator in the electromagnetic pump (e.g., relative to a coil thereof or other structure of pump). Yet further, other embodiments relate to infusion devices for delivery of infusion medium (e.g., implantable infusion devices) or other medical devices that may employ electromagnetic pumps utilizing the techniques described according to the present invention.

In general, one or more embodiments according to the present invention use both the electrical potential applied to a coil of an electromagnetic pump and the current passing through the coil, as well as the mathematical relationship between them, and the changing inductance, to provide reliable detection of end of stroke and, also, in one or more embodiments, provide stroke positioning information. Various algorithms are described herein to provide information for the detection of the end of a pump stroke, and, also, in one or more embodiments, information related to such a pump stroke (e.g., position information of the actuator of the pump). For example, such algorithms may be referred to herein as a first flux derivative algorithm (e.g., for use in detection of end of pump stroke), back electromotive force (back EMF) algorithm (e.g., for use in detection of end of pump stroke), and coil inductance variation algorithm (e.g., for use in detection of position of the actuator of the pump).

Figure 1:
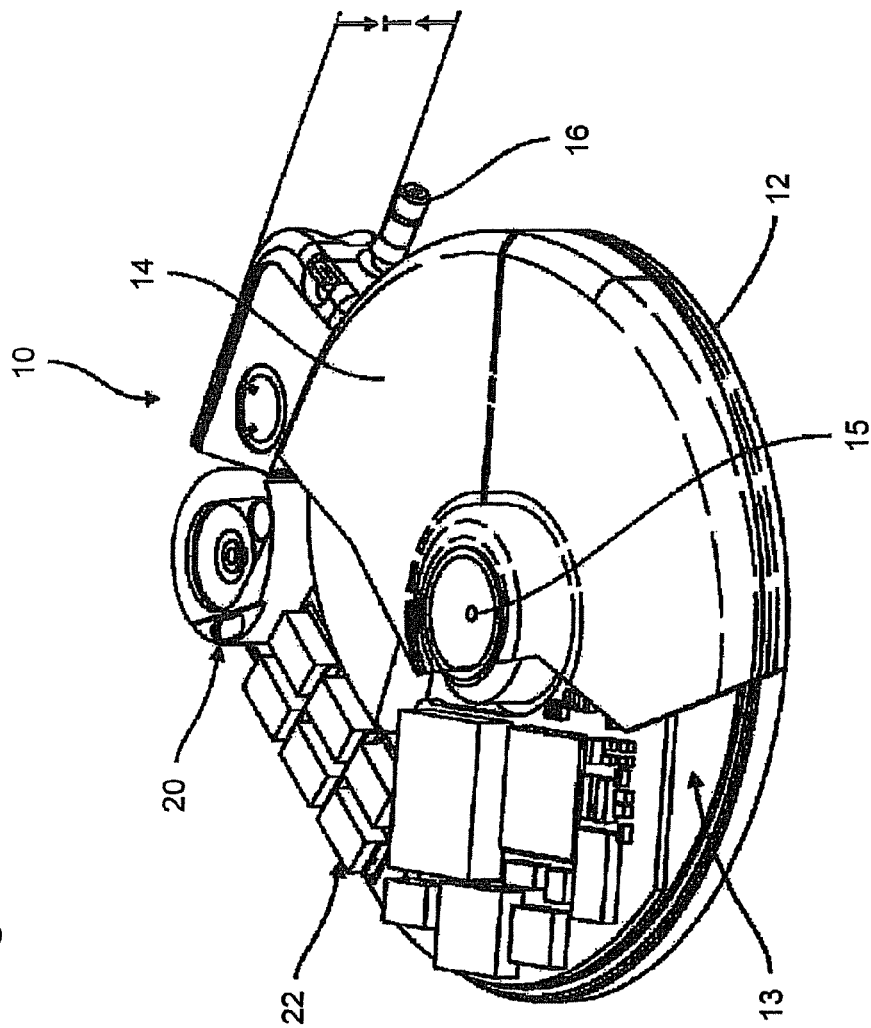
FIG. 1 is a perspective view of an implantable infusion device according to one embodiment of the present invention.

FIG. 1 shows one embodiment of an implantable infusion device 10 according to the present invention. The illustrative infusion device 10 is configured to be surgically implanted into a patient. A catheter may be connected to the pump so as to deliver infusion medium to a patient, for example, by feeding infusion medium to a particular target site (e.g., location in the venous system, within the spinal column, or in the peritoneal cavity) of the patient.

As described herein, one or more embodiments of the present invention may be configured for enhancing implantability and prolonged usage once implanted (e.g., battery life). Further, one or more embodiments may be implemented as external infusion devices, which connect to patients through suitable catheter devices, or the like.

Further, one or more embodiments may be used in other contexts for delivery of a medium into other suitable environments. Therefore, for purposes of simplifying the present disclosure, the term patient is used herein to refer to the entity or environment in which an implantable device is implanted or to which an external device is connected. Also, the term "infusion medium" is used herein to refer to any suitable medium delivered by the device 10 (e.g., medicaments, drugs, treatment medium, etc.).

The illustrative device 10 is configured as a single unit, containing, for example, an infusion medium reservoir, a pump mechanism, and an electronic control system, in a single relatively compact package or housing 12. However, other embodiments may employ reservoirs, pump mechanisms, power sources, and control systems in multiple discrete units operatively connected together by suitable conduits.

The infusion device 10 includes a generally disc-shaped housing 12. While a generally circular disc-shaped embodiment is illustrated in FIG. 1, it will be understood that further embodiments of the invention may employ housings of other shapes including, but not limited to, oval, oblong, rectangular, or other curved polygonal shapes. In implantable device embodiments, the housing 12 is made of a biocompatible material and is relatively small to reduce or minimize patient trauma during implant surgery and after implantation.

The housing 12 includes a reservoir housing portion 13 containing a reservoir for holding a volume of infusion medium, such as, but not limited to, a liquid medication to be administered to a patient. The housing 12 includes a further housing portion 14 located above the reservoir housing portion 13, in the orientation shown in FIG. 1, for containing an electromagnetic pump 20 and an electronic control system 22 (e.g., power source and control electronics) as described herein. One will recognize that various types of housings and reservoirs may be utilized according to the present invention and the present invention is not limited to the illustrative housings and reservoirs shown herein.

The housing 12 has an outlet 16 through which the infusion medium may be expelled. When the device 10 is implanted in a patient or connected externally to a patient, a catheter may be connected to the outlet 16 through which infusion medium may be expelled (e.g., into the patient's bloodstream or to a selected location of the patient's body).

Infusion device 10 also includes an inlet structure 15 which provides a closeable and sealable fluid path to the reservoir and the reservoir housing portion 13 of the housing 12. For example, the inlet structure provides a port for receiving a needle through which fluid may be transferred to the infusion device 10, for example, to fill or refill the reservoir of the device. One or more various different configurations of inlet and outlet structures may be employed according to the present invention, and the present invention is not limited to any particular inlet and outlet structure.

The infusion device 10 includes an electromagnetic pump 20 (e.g., a drive mechanism) and an electronic control system 22 located in a housing portion 14. The electromagnetic pump 20 is connected between the reservoir in the reservoir housing portion 13 and the outlet 16. The electronic control system 22 includes a power source, such as a battery, and control electronics for controlling the electromagnetic pump 20 to deliver infusion medium from the reservoir to a patient in a selected manner. The electromagnetic pump 20 may be controlled to deliver infusion medium in any suitable manner, for example, according to a programmed dispensing rate or schedule, or according to an actuation signal from a sensor, timer, or other suitable source.

For example, according to one or more embodiments herein, the electromagnetic pump 20 provides delivery of infusion medium by employing a plurality of pump strokes to drive the infusion medium to the outlet 16 of the device. Such pump strokes of the electromagnetic pump 20 are controlled using control electronics of the electronic control system 22 according to the present invention (e.g., controlled at least in part with detection of end of pump stroke).

As described herein, a number of techniques relating to electromagnetic pump configurations and operation are described herein to enhance the efficient use of power. One or more of such techniques, or features, may be employed in various embodiments of the present invention. For example, detection of end of pump stroke may be used to determine the proper time to de-energize the coil of the electromagnetic pump (e.g., cut off power to the pump upon detection of the end of a pump stroke).

In one or more embodiments, the infusion device 10 is configured such that once implanted, it functions for a relatively long period of time to administer infusion medium to a patient and periodically be replenished from outside of the patient's body. The operational life of the infusion device 10 is, however, limited in part by the capacity of its power source and the power requirements of the device.

In one or more embodiments, the electromagnetic pump 20 of the infusion device 10 is employed to provide reliable pumping action and the operation thereof is controlled to be highly efficient with respect to power consumption. As such, the operational life of the infusion device is improved. Further, electromagnetic pumps controlled according to the present invention provide highly efficient use of power, as described herein, and as such may be operated with smaller power sources (e.g., power sources including relatively smaller batteries), which can allow the infusion device to be made smaller.

Generally, electromagnetic pumps employ electromagnetic and mechanical forces to move between retracted (or quiescent) and forward stroke states to cause infusion medium to be drawn from a reservoir, through a pump inlet, and forced out of a pump outlet. Such electromagnetic forces are generated by the application of an electrical power signal to a coil of the electromagnetic pump which, when energized, operates on an actuator to provide a pump stroke. For example, the actuator may include an armature and a piston. In a retracted state, the actuator is mechanically urged towards a retracted position. When the coil is energized, the actuator moves to a forward stroke position. The movement of the actuator between retracted and forward states creates pressure differentials within the internal chambers and volumes of the electromagnetic pump to draw infusion medium from the reservoir into the pump inlet and drive medium out of the pump outlet.

In one or more embodiments of the present invention, lowering the power consumption requirements of the electromagnetic pump employs the detection of the end of a pump stroke such that power is not unnecessarily provided to the electromagnetic pump. In other words, upon detection of the end of a pump stroke, power to the electromagnetic pump can be turned off, as opposed to applying power to the electromagnetic pump after the pump stroke has ended (e.g., after which little or no infusion medium is driven out of the pump outlet).

One exemplary electromagnetic pump 20 shall be described in further detail with reference to FIG. 2 so as to give context to control techniques described herein with respect to electromagnetic pumps. For example, such an electromagnetic pump 20 is described in detail in U.S. Pat. No. 6,997,921 B2 to Gray et al. issued 14 Feb. 2006, and entitled "Infusion device and driving mechanism for same," which is incorporated herein by reference. This is but one example of a type of electromagnetic pump for which the control techniques described herein, including detection of end of pump stroke and determination of position information, may be employed.

One will recognize that various other embodiments may employ other suitable electromagnetic pumps (e.g., other drive mechanism configurations). Such control techniques as described herein may be employed, at least in one or more embodiments, with any electromagnetic pump that includes a coil that can be energized to produce a pump stroke, wherein an actuator is moveable in response to the energization of the coil, for example, to drive, or otherwise move, a medium from one location to another. However, the present invention is not limited to any particular electromagnetic pump configuration.

FIG. 2 shows the electromagnetic pump 20 according to one exemplary embodiment of the present invention. In this illustrated embodiment, the electromagnetic pump 20 has a partially cylindrical, disc-shaped configuration with extended corners 24 and 25. An inlet 27 is provided at the corner 24 and an outlet 28 is provided at the corner 25. The inlet 27 may be connected in flow communication with the reservoir portion 13 of the infusion device 10, as shown in FIG. 1, through suitable conduit (not shown) within the infusion device 10. Similarly, the outlet 28 may be connected in flow communication with the outlet 16 of the infusion device 10, as shown in FIG. 1, through suitable conduit (not shown) within the infusion device 10.

Figure 4:
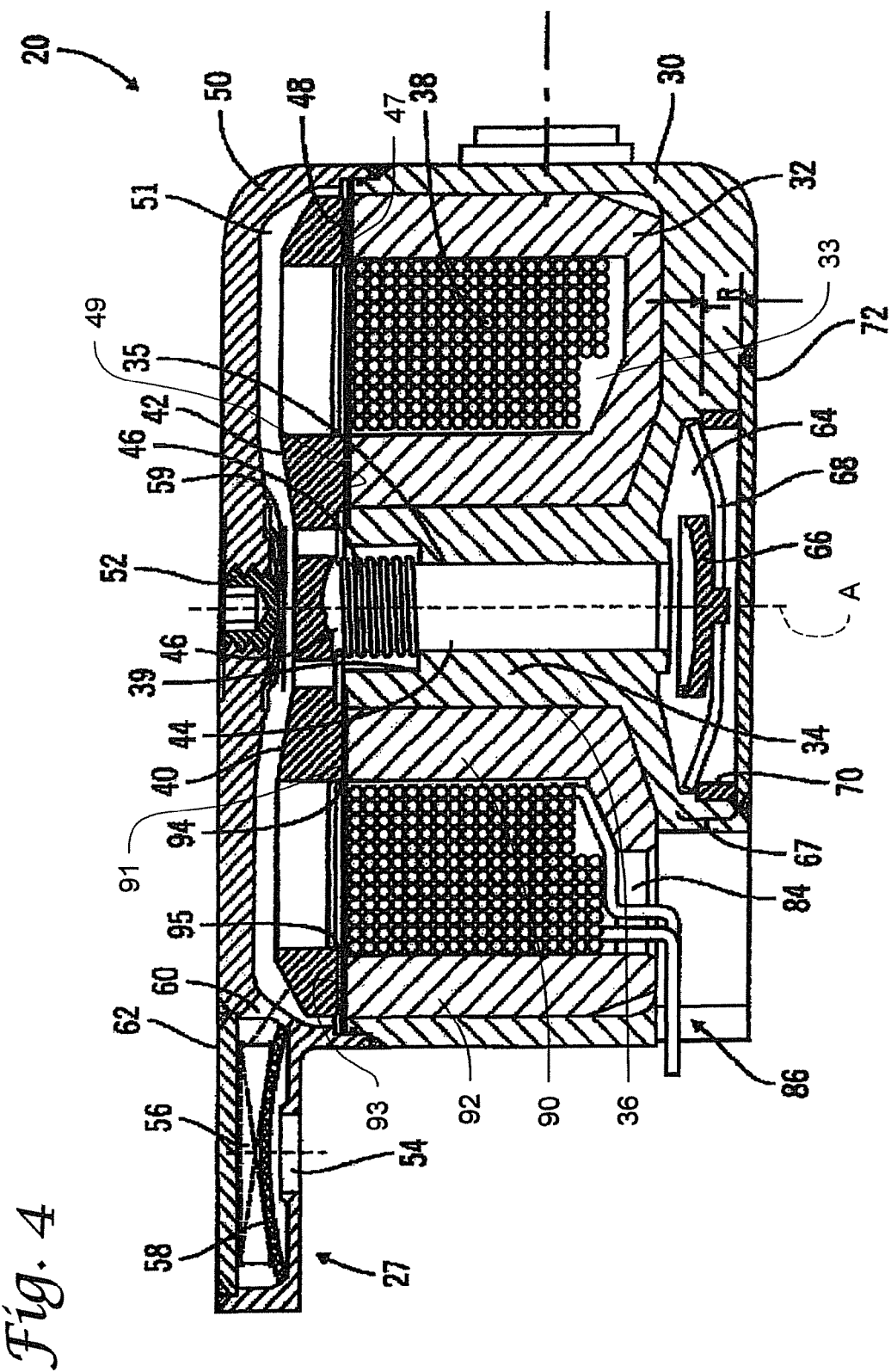
FIG. 4 is a cross-section view of the exemplary electromagnetic pump embodiment of FIG. 3, in a forward stroke position or state.

FIG. 3 shows a cross-sectional view of one exemplary embodiment of the electromagnetic pump 20 in a retracted position or state. FIG. 4 shows a cross-sectional view of the same electromagnetic pump 20 embodiment in a forward position or state. As described in more detail herein, the electromagnetic pump 20 employs electromagnetic and mechanical forces to change (or move) between retracted and forward states to cause infusion medium to be drawn in through inlet 27 and forced out of the outlet 28.

As shown in the figures, the electromagnetic pump 20 includes a housing member 30 that has a central hub portion 34 with a central piston channel 35. The bottom side of the housing member 30 (with reference to the orientation shown in FIGS. 3 and 4) includes an opening through which coil wires may pass, as described herein. The bottom side of the housing member 30 also includes a configuration of recesses and cavities for providing an outlet chamber, an outlet passage, and, in one or more embodiments, for example, accumulator chambers. The housing member 30, in one or more embodiments, is formed of rigid, biocompatible, and infusion medium compatible material, having no or low magnetic permeability, such as, but not limited to, titanium, stainless steel (which may be ferritic or non-ferritic), biocompatible plastic, ceramic, glass, or the like.

As shown in FIGS. 3 and 4, a coil cup 32 is located within the annular interior section of the housing 30. The coil cup 32 has a generally cylindrical shape, open on one end to a hollow annular interior 33. The coil cup includes an inner annular wall 90 having an end surface 91 (or inner pole surface). The coil cup 32 has an outer wall 92 having an end surface 93 (or outer pole surface). The outer wall 92 is connected to the inner wall 90 by a backiron portion of the cup 32. As described further herein, at the open end of the cup member, the end surfaces 91 and 93 of the inner and outer walls 90 and 92, define pole surfaces that cooperate with pole surfaces on an actuator 40 to provide a path for electromagnetic flux during a forward stroke of the electromagnetic pump.

As assembled, the coil cup 32 is located in the hollow interior of the housing member 30, with a central portion 34 of the housing 30 extending through the piston channel 36 of the coil cup 32, as shown in FIGS. 3 and 4. A coil 38 is located within the hollow, annular interior of the coil cup 32 and is disposed around the axis A of the annular interior of the coil cup 32. The coil cup 32 is provided with an opening 84 through which coil leads 86 extend, as shown in FIGS. 3 and 4.

The coil cup 32 is preferably made of a generally rigid material, having a relatively high magnetic permeability such as, but not limited to, low carbon steel, iron, nickel, ferritic stainless steel, ferrite, other ferrous materials, or the like. The coil 38 comprises a conductive wire wound in a coil configuration. The coil wire may include any suitable conductive material such as, but not limited to, silver, copper, gold, or the like, with each turn electrically insulated from adjacent turns in the housing. In one preferred embodiment, the coil wire has a square or rectangular cross-section to allow minimal space between windings, thereby allowing a greater number of coil turns and, thus, improved electrical efficiency.

The electromagnetic pump 20 also includes an actuator 40. The actuator 40 includes an armature portion 42 and a piston portion 44. The actuator is preferably made of a generally rigid, biocompatible, and infusion medium compatible material, having a relatively high magnetic permeability such as, but not limited to, ferrous materials, ferritic stainless steel with high corrosion resistance, or the like.

One will recognize that in accordance with the present invention any type of coil and actuator configuration forming the electromagnetic pump may benefit from the control techniques described according to the present invention. As such, the present invention is not limited to any particular coil or actuator configuration.

The armature 42 of the actuator, as shown in the illustrative embodiment of FIGS. 3 and 4, cooperates with the inner and outer walls 90, 92 of the coil cup 32 to provide a flux path for electromagnetic flux. The spacing between the pole surfaces on the armature 42 and the pole surfaces on the walls of the coil cup 32 define gaps in the flux path.

With reference to FIGS. 3 and 4, the actuator 40 is arranged with the piston portion 44 thereof extending through the axial channel 35 of the housing 30 and with the armature portion 42 positioned adjacent the open side of the coil cup 32. An actuator spring 46 is positioned to force the armature portion 42 of the actuator 40 in the direction away from the open side of the coil cup 32 to provide a gap between the armature 42 and the open side of the coil cup 32. A biocompatible and infusion medium compatible barrier 48 is located over the open side of the coil cup 32, between the armature 42 and the coil cup 32, to maintain a gap between those two members and/or to help seal the annular interior of the coil cup 32 and coil 38.

The actuator spring 46 in the illustrated embodiment comprises a coil spring disposed around the piston portion 44 of the actuator 40 adjacent the armature portion 42. One end of the coil spring abuts the armature portion 42 of the actuator, while the opposite end of the coil spring abuts a shoulder 39 in the piston channel 35 of the housing 30. In this manner, the actuator spring 46 imparts a spring force between the housing and the actuator 40 to urge the actuator towards its retracted position in FIG. 3.

The electromagnetic pump 20 further includes a cover member 50 which attaches to the housing member 30, over the open side of the housing member 30 and the barrier 48. The cover member 50 is preferably made of generally rigid, biocompatible, and infusion medium compatible material, having a relatively low magnetic permeability (being relatively magnetically opaque) such as, but not limited to, titanium, stainless steel, biocompatible plastic, ceramic, glass, or the like.

The cover member 50 defines an interior volume 51 between the barrier 48 and the inner surface of the cover member 50. The armature portion 42 of the actuator 40 resides within the interior volume 51 when the cover 50 is attached to the housing 30, such as shown in FIGS. 3 and 4. As described below, the actuator 40 is moveable in the axial direction within the volume 51, between the retracted position shown in FIG. 3 and a forward stroke position shown in FIG. 4. This movement is created by the action of electromagnetic force generated when a current is passed through the coil 38 and the mechanical return action of the actuator spring 46 (e.g., a pump stroke).

An adjusting plunger 52 is located within the cover 50 for contacting the armature portion 42, when the armature portion is in the fully retracted position shown in FIG. 3, and to set the retracted or retracted position of the armature. In one or more embodiments, a seal may be disposed between the plunger 52 and the cover member 50, for example, a flexible diaphragm 59 may be coupled to the inside surface of the cover 50 and sealed around the opening through which the plunger 52 extends.

The cover member 50 includes the inlet 27 of the electromagnetic pump 20 which has an inlet opening 54 in fluid flow communication with the interior volume 51, as described herein. The inlet opening 54 connects in fluid flow communication with the reservoir of an infusion device 10 (FIG. 1) to receive infusion medium from the reservoir. Connection of the inlet opening 54 and the reservoir may be through any suitable conduit.

The inlet opening 54 provides a flow to an inlet chamber 56 formed in the cover member 50 adjacent the inlet opening. A filter or screen member, such as a porous or screen material 58, may be disposed within the inlet chamber 56 between the inlet opening 54 and inlet port 60 to the volume 51. A one-way inlet valve (not shown) to allow medium to flow into but not out of the interior volume 51 through the inlet opening 54 may also be provided in the flow path between the inlet opening 54 and the inlet port 60, or within inlet port 60. Further, the cover member 50 may be provided with an inlet cover 62 that, when removed, allows access to the inlet chamber 56.

As shown in FIGS. 3 and 4, the piston portion 44 of the actuator 40 extends through the axial channel 35 in the housing 30, toward an outlet chamber 64 at the end of the axial channel 35. The channel 35 has an inside diameter which is larger than the outside diameter of the piston portion 44. As a result, an annular volume is defined between the piston portion 44 and the wall of the axial channel 35, along the length of the axial channel 35. Infusion medium may flow through the annular volume, from the volume 51 within the cover 50 to a piston chamber 65 located between the free end of the piston portion 44 and a valve member 66 of a valve assembly 67. In one or more embodiments, the radial spacing between the piston portion 44 and the wall of the axial channel 35 is selected to be large enough to provide a suitable flow toward the piston chamber 65 to refill the piston chamber 65 (during a return stroke of the piston portion), but small enough to sufficiently inhibit backflow of medium from the piston chamber 65 (during a forward stroke of the piston portion).

The valve assembly 67 in the embodiments of FIGS. 3 and 4 includes the valve member 66, a valve spring 68, and support ring 70. The valve member 66 is located within the outlet chamber 64 and, as shown in FIG. 3, is positioned to close the opening between the axial channel 35 and the outlet chamber 64 when the actuator 40 is in the retracted position. In FIG. 4, the valve member 66 is positioned to open a flow passage between the axial channel 35 and the outlet chamber 64. The valve spring 68 is located within the outlet chamber 64 to support the valve member 66. Spring 68 imparts a spring force on the valve member 66 in the direction toward piston 44, urging the valve member 66 toward a closed position to block the opening between the axial channel 35 and the outlet chamber 64. The valve spring 68 is spaced from a valve cover 72 by a ring 70. The valve cover 72 is sealed to the housing 30 to enclose the outlet chamber 64. The ring 70 and spring 68 characteristics are such that sufficient forces urge the valve member 66 into a suitably sealed or closed position, as shown in FIG. 3, yet allow the movement force of the piston portion 44 (caused by electromagnetic force generated by the coil) to overcome the spring force and open the valve member 66, as shown in FIG. 4.

In operation, the electromagnetic pump 20 employs electromagnetic and mechanical forces to move between retracted (FIG. 3) and forward (FIG. 4) positions to cause infusion medium to be drawn into and driven out of electromagnetic pump 20 in a controlled manner. The electromagnetic pump 20 is controlled by an electronic control system, such as electronic control system 22 as shown in the infusion device in FIG. 1, and of which illustrative embodiments shall be described with reference herein to the general diagram of FIG. 5.

In the retracted position, the spring 46 urges the actuator 40 toward its retracted position shown in FIG. 3. When the coil 38 is energized to overcome the spring force of spring 46, the actuator 40 moves to its forward stroke position shown in FIG. 4. The movement of the actuator 40 between retracted and forward positions creates pressure differentials within the internal chambers and volumes of the electromagnetic pump 20 to draw medium into the inlet 27 and drive medium out of the outlet 28.

For example, when the coil 38 is deactivated (not energized or not energized in a manner to overcome the spring force of spring 46), the actuator 40 is held in its retracted position (FIG. 3) under the force of spring 46. When the coil is deactivated immediately following a forward stroke, the spring 46 moves the actuator 40 to the retracted position of FIG. 3 from the forward position shown in FIG. 4. Openings in the armature portion 42 of the actuator 40 provide passage for medium to pass and, thus, reduce viscous drag on the actuator 40.

As the actuator 40 retracts, the piston portion 44 of the actuator 40 is retracted relative to the valve member 66, such that a piston chamber 65 volume is formed between the end of the piston portion 44 and the valve member 66. The formation of the piston chamber 65 volume creates a negative pressure which draws infusion medium from the volume 51 of the cover member 50, through the annular space between the piston portion 44 and the wall of the channel 35, and into the piston chamber 65.

In the retracted position, a gap is formed between each of the annular pole surfaces 91 and 93 separated by the inner and outer walls 90 and 92 of the coil cup 32 and the respective annular surfaces of the inner and outer pole sections 49 and 47 of the actuator's armature portion 42. In particular, with reference to FIG. 3, a first gap 94 is formed between the annular pole surface 91 of the inner cup wall 90 and the annular surface of the inner pole section 49. A second gap 95 is formed between the annular surface 93 of the outer cup wall 92 and the annular surface of the outer pole section 47.

When the coil 38 is energized, the actuator 40 is forced in the direction to close the gaps 94 and 95 and moves to its forward position (FIG. 4) under the influence of electromagnetic flux generated by the energized coil. In particular, the coil may be energized by passing electrical current through the coil conductor to create electromagnetic flux. This current is created by application of an electrical potential provided by a power source (e.g., discharge of a capacitor).

The electromagnetic flux defines a flux path through the coil cup walls, across the gaps 94 and 95, and through the armature portion 42 of the actuator 40. The electromagnetic flux provides an attraction force between the annular surfaces 91 and 93 of the coil cup 32 and the annular surfaces 47 and 49 of the armature portion 42 to overcome the spring force of spring 46 and draw the armature 42 toward the coil cup 32. As the armature portion 42 of the actuator is drawn toward the coil cup 32, the piston portion 44 of the actuator is moved axially through the channel 35 in the direction toward the outlet chamber 64.

With the coil energized, the piston portion 44 continues to move under the action of the armature portion 42, until a mechanical stop is reached, for example, mechanical contact of the actuator 40 with barrier 48, a portion of the housing 30, or cover member 50. Under some circumstances (e.g., when a catheter connected to the outlet is blocked), the motion of the armature portion may only continue until the back pressure of the fluid overcomes the electromagnetic force provided by energizing the coil 38 (e.g., an incomplete delivery of medium). The present invention provides one or more various techniques for detecting the end of a pump stroke, or, in other words, for example, when the piston portion 44 stops moving by a mechanical stop.

The movement of the piston portion 44 towards the stopping point reduces the volume of the piston chamber 65 and increases the pressure within the piston chamber until the pressure is sufficient to overcome the force of the valve spring

68. As the valve spring force is overcome by the pressure within the piston chamber, the valve member 66 is moved toward an open position, away from the opening between the piston chamber 65 and outlet chamber 64. When the valve member 66 is in the open position, medium is discharged through the outlet chamber 64 and outlet 28 (see FIG. 2).

When the coil is deactivated (e.g., power is removed from the coil) and the piston portion 44 is moved back to its retracted position, the pressure in the piston chamber 65 reduces, and the valve member 66 is reseated under the action of valve spring 68. This prevents fluid from flowing back into the electromagnetic pump, through the outlet 28. In addition, a negative pressure is created in piston chamber 65 to draw medium into the chamber for the next forward pump stroke.

In this manner, energization of the coil 38 to move the actuator 40 to its forward position (FIG. 4) causes a measured volume of medium to be discharged through the outlet 28. As described herein, when the coil 38 is de-energized, the actuator 40 is returned to the retracted position (FIG. 4) under the force of spring 46, and an additional volume of medium is drawn into the piston chamber 65 for the next discharging operation. Accordingly, the coil 38 may be energized and de-energized by a controlled electronic signal, where the control signal actuates electromagnetic pump 20 to discharge a measured volume, or bolus, of medium. The controlled electronic signal, in one or more embodiments of the present invention, is provided by an electronic control system such as that shown generally in FIG. 1, and of which one or more embodiments are described further with reference to FIG. 5.

When the actuator 40 is stopped, for example, by mechanical stop structure, or in any other manner, the coil current/voltage relationship changes. In the present invention, control electronics are provided to detect the end of the pump stroke based on sensed electrical characteristics associated with the electromagnetic pump 20.

Figure 5:
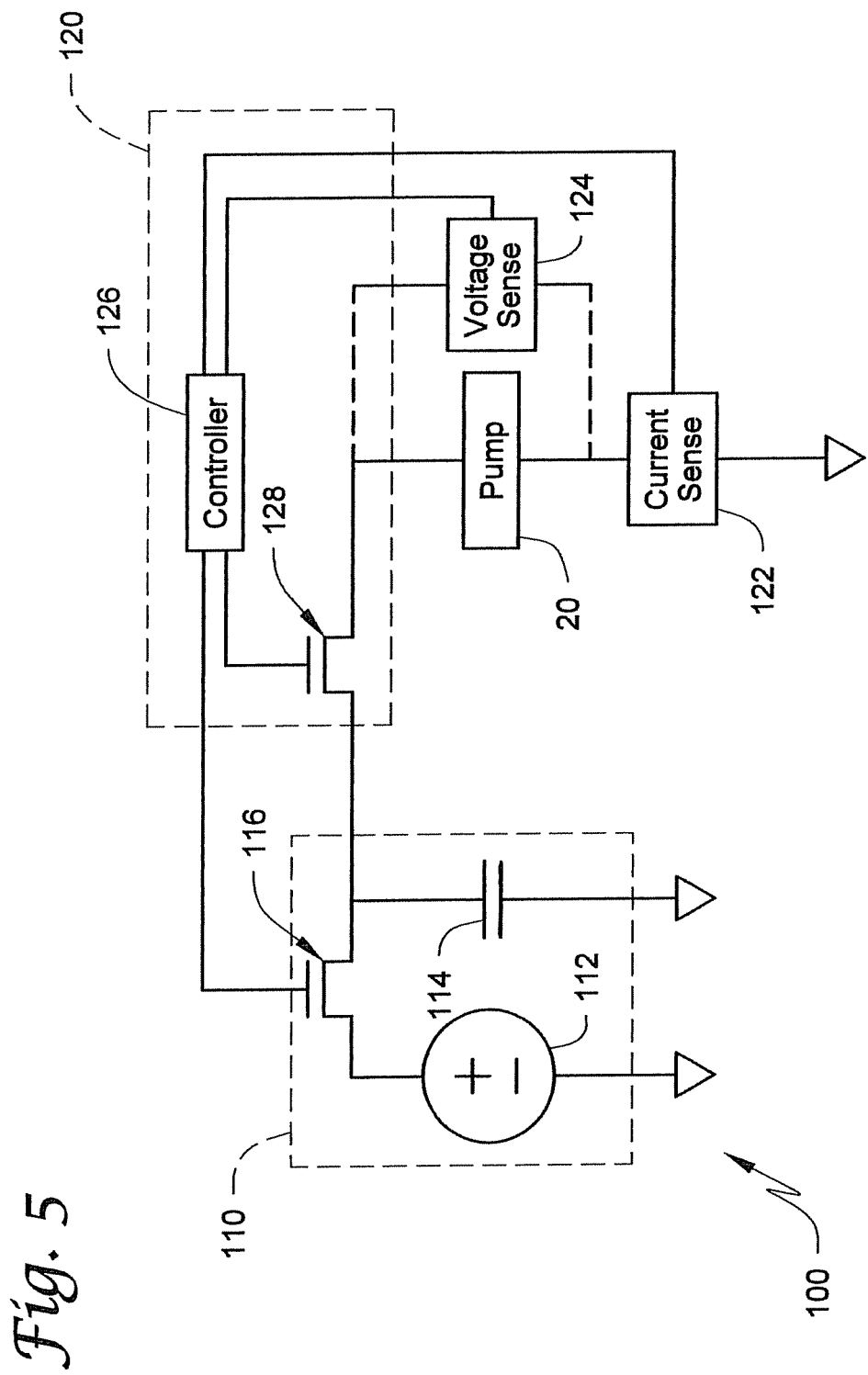
FIG. 5 is a generalized block diagram of one exemplary embodiment of an electromagnetic pump, power source, and control electronics according to the present invention.

In one or more embodiments according to the present invention, control electronics (e.g., such as those shown and described herein with reference to FIG. 5) are connected to detect the end of a pump stroke (e.g., using a first flux derivative algorithm or a back EMF algorithm). When such detection occurs, the coil 38 may be de-energized. In this manner, the coil 38 may be energized for only as long as the electromagnetic flux generated by the coil 38 is providing useful work. Once the actuator motion is stopped at the end of the pump stroke, and no further useful work is provided by the electromagnetic flux, the coil 38 may be deactivated to reduce or minimize power consumption requirements of the electromagnetic pump 20.

FIG. 5 shows a generalized block diagram of an illustrative embodiment of an electronic control system 100 that may be connected to the electromagnetic pump 20 for control thereof. The electronic control system 100 includes a power source 110 connected to selectively energize the coil of the electromagnetic pump 20, wherein the power source 110 applies a source electrical potential to the coil to pass a coil current therethrough.

The electronic control system 100 further includes control electronics 120 for receiving one or more sensed signals to be used in the detection of the end of a pump stroke. The control electronics 120 includes a controller 126 for controlling a switch device 128 to energize and de-energize the electromagnetic pump 20. The control electronics 120 further include a current sense device 122 and a voltage sense device 124 for providing information to controller 126 for use thereby in detection of the end of a pump stroke.

In one or more embodiments, the power source 110 includes a power supply 112 connected to a capacitor 114 for charging the capacitor 114. Further, in one or more embodiments, the power source 110 includes a power supply 112 operatively connected via a switching device 116 to a capacitor 114 for selectively charging a capacitor 114 under control of the control electronics 120.

In one or more embodiments, the power supply 112 is connected to charge the capacitor 114, and the capacitor 114 is connected to selectively discharge power to the coil of the electromagnetic pump 20. The charged capacitor 114 can provide a generally fast response power pulse to the coil, on command or when otherwise desired.

The electronic control system 100, including the control electronics 120, may be implemented, for example, on a single circuit board, or in any other manner. For example, in one or more embodiments, the electronic control system may be implemented with the components as discrete units, and electrically connected together for operation.

In one or more embodiments, the power source 110 includes a portable, depletable power storage device, such as a battery. The use of portable power supplies, such as batteries, may be advantageous in the context of the application, such as when the electromagnetic pump is intended to be portable (e.g., in implanted or portable external infusion devices). However, in one or more other embodiments, other forms of power sources suitable for other applications, including non-portable and non-depleting power sources, may be employed.

Control electronics 120 control the charging and discharging of the capacitor 114 and provide one or more additional functions as described herein. For example, control electronics 120 provide for the operation of any detection processes as well as determination processes described herein. The control electronics 120 may comprise one or more programmable processors, logic circuits, or other hardware, firmware, or software components configured for implementing functions as described herein. One will recognize that various embodiments may be employed using suitable hardware, firmware, or programmable processor implementations to accomplish the functions described herein carried out by control electronics 120.

The control electronics 120 control the discharge of power from the capacitor 114 to the coil of the electromagnetic pump 20, as needed or desired for operating the electromagnetic pump 20, by selectively coupling or decoupling the capacitor 114 to the coil thereof. As shown in FIG. 5, the capacitor 114 is connected to the coil of the electromagnetic pump 20 through an electronic switch device 128 of the control electronics 120.

One will recognize that any suitable switch device capable of providing such connection may be used according to the present invention. For example, in one or more embodiments, the switch device may take the form of a field effect transistor (FET) or a junction transistor that is controlled, for example, by controller 126, to close and/or open when commanded. One will recognize that any suitable electronic or electromagnetic switch configurations, junction transistors, relays, or the like, may be employed as the switch device 128. For example, by applying a control signal to the switch device 128, the switch device 128 may be closed to connect the capacitor 114 to the coil and allow the capacitor 114 to discharge.

Controller 126 may also provide a control signal for operating a switch device 116 located between the power supply 112 and the capacitor 114 to selectively control the charging of the capacitor 114 by the power supply 112. The switch device 116 may be of any suitable form, such as described herein with respect to switch device 128, and, in one or more embodiments, may be a FET device. By applying a suitable signal to the switch device 116, the switch device 116 may be selectively closed to charge the capacitor 114 or selectively opened to terminate such charging.

The control electronics 120 may be programmed or otherwise configured to generate signals to control the opening or closure of switch device 128 upon the occurrence of one or more various events. For example, switch device 128 may be closed upon the need for delivery of an infusion medium into the infusion environment (e.g., initiate a pump stroke to deliver the infusion medium). Further, for example, such events may include opening the switch device 128 upon the expiration of a predetermined time period if, for example, detection of an end of pump stroke does not occur. Yet further, for example, switch device 128 may be closed to initiate a pump stroke and opened upon detection of an end of pump stroke. One will recognize that any number of events may occur to control pumping action by the electromagnetic pump 20 as determined by the control electronics 120.

Upon closure of the switch device 128, as shown in FIG. 5, the capacitor 114 is electrically coupled to the coil of the electromagnetic pump 20. If the capacitor 114 is charged when the switch device 128 closes, the charged capacitor 114 would discharge to energize the coil of the pump 20. As described herein, when the coil is energized, the electromagnetic pump actuator is caused to move to a forward position, for example, against a mechanical spring force. The actuator may abut a stop surface or the like at the actual end of the forward stroke, or, in other words, fail to move any further in a forward direction as a result of a back force on the piston of the actuator of the electromagnetic pump 20.

Upon opening of the switch device 128, the capacitor 114 is electrically decoupled from the coil of the electromagnetic pump 20. After the switch device 128 is opened, energy in the coil dissipates and the mechanical spring force returns the actuator of the electromagnetic pump to its retracted position. The switch device 116 may then be closed to allow the capacitor 114 to recharge for subsequent pump stroke operation. In this manner, the capacitor 114 is controlled to charge and discharge to provide electrical energy to the coil of the pump 20 as needed to effect a pump stroke operation (e.g., a plurality of pump strokes).

Figure 6:
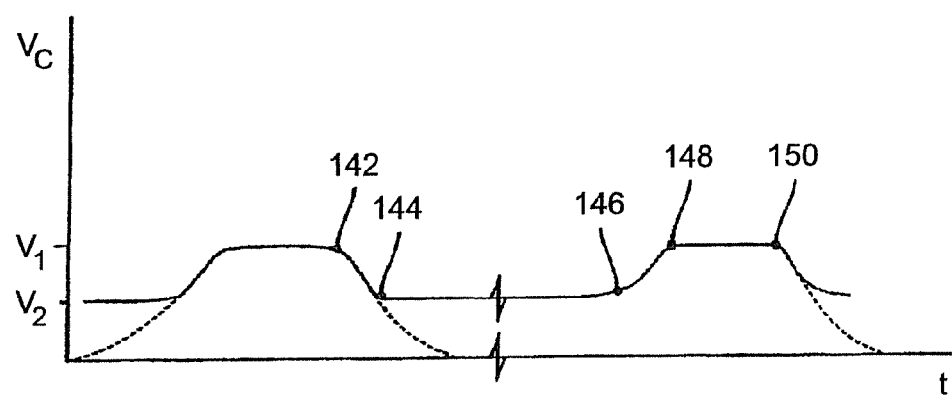
FIG. 6 is a graphical diagram of exemplary voltage characteristics of a power discharge capacitor controlled according to one embodiment of the present invention.

A graph of an example voltage diagram for a capacitor 114 is shown in FIG. 6. With reference to FIG. 6, the voltage $V_c$ across the capacitor 114 (i.e., source voltage $U_{source}$ across the capacitor 114) rises during charging to its fully charged level $V_1$ from its previously charged level $V_2$. To effect a pump stroke operation, a control signal is provided by the control electronics 120 to turn on switch 128 at point 142 in FIG. 6.

Once the switch device 128 is closed (i.e., turns on), the capacitor 114 discharges and the source voltage $U_{source}$ or voltage $V_c$ across the capacitor drops. However, prior to the capacitor 114 reaching a fully discharged state, the control electronics 120 detects an end of pump stroke and opens (i.e., turns off) the switch device 128, for example, at point 144 in FIG. 6. The broken line portion of FIG. 6 shows the voltage across the capacitor 114 had the switch device 144 remained closed to completely discharge the capacitor. However, because the switch device 128 is opened prior to full discharge of capacitor 114, the source voltage across the capacitor remains at level $V_2$, above the fully discharged level.

While some leakage may occur before the next charging operation, the voltage across the capacitor 114 is at about the level $V_2$ or slightly lower, at point 146 in FIG. 6, when switch 116 is closed to recharge the capacitor 114. Once the capacitor 114 is fully charged, as shown at point 148 in FIG. 6, the switch 116 may be opened and, as shown at point 150, the switch 128 may be closed to effect another pump operation. Thus, by controlling the capacitor to discharge partially, but not fully, for each pump stroke operation, the voltage across the capacitor 114 may have characteristics similar to that shown in FIG. 6.

Because the voltage $V_c$ across the capacitor 114 remains at or about the level. $V_2$ (above the fully discharged level) after its discharge during a pump stroke, the amount of energy needed to recharge the capacitor 114 to the level $V_1$ is less than would be required had the capacitor 114 been fully discharged. By selecting the size of the capacitor 114 and the levels $V_1$ and $V_2$, suitable power may be provided to the coil of the electromagnetic pump 20 during the discharge (between points 142 and 144) to effect a pump stroke operation, while significant power savings may be achieved during the recharging period (between points 146 and 148) as compared to charging a fully discharged capacitor. As such, detection of the end of the pump stroke such that control electronics 120 may open switch device 128 and de-energize the coil of the electromagnetic pump 20 is important to reducing power consumption.

In other words, if detection of pump stroke does not occur, discharge may continue until the capacitor is fully discharged, or until a time-out corresponding to a time when it is known that the pump stroke would be completed. In such situations, energy may be wasted. In other words, if the capacitor 114 continues to discharge power to the coil of the electromagnetic pump 20 after the actuator reaches the end of its stroke, such continued discharge of power will not produce any further movement of the pump actuator and, thus, will be wasted. As such, according to one or more embodiments of the present invention, the point at which the capacitor 114 stops discharging power to the coil of the electromagnetic pump 20 is controlled to occur at the detection of the end of the actual stroke of the pump 20.

However, in one or more other embodiments, detection of the end of pump stroke according to the present invention may be used for one or more other applications. For example, such detection may be used to terminate the discharging of power to the coil at a time prior to the actual end of the pump stroke.

Figure 7:
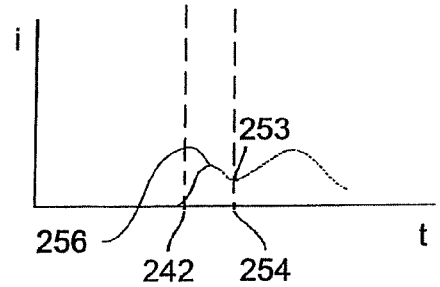
FIG. 7 is a graphical diagram of exemplary current characteristics of a coil connected to a power discharge capacitor controlled according to one embodiment of the present invention.

FIG. 7 shows a graphical representation of the coil current during a pump stroke. In FIG. 7, the solid line represents current passing through the coil of the electromagnetic pump 20. The current graph of FIG. 7 shows the point 242 at which the capacitor 114 begins discharging current to the coil. A period of time prior to point 242 may involve a circuit warm-up period. Point 254 in FIG. 7 represents the time in which the capacitor 114 is cut off.

A capacitor cut off point 254 is determined by the detection of the end of the pump stroke. As shown in FIG. 7, a sharp rise (or inflection) or a change in direction of the current graph of FIG. 7 indicates actuator deceleration that occurs at the actual end of the pump stroke. As such, such a current inflection in the coil current waveform could be detected by control electronics 120 so as to provide an indication of the end of stroke for use in opening switch 128 and de-energizing the coil of electromagnetic pump 20. The current through the coil may be provided to control electronics 120 by a current sense device 122 as shown in FIG. 5.

However, in one or more circumstances, the current waveform tends to be sensitive to the inflection point shape and also tends to be difficult to detect when the capacitor discharges. Note, however, that the current through the coil reaches a peak 256 during capacitor discharge and prior to the inflection point 253 of a pump stroke.

The control electronics 120, according to the present invention, uses the sensed coil current (e.g., sensed using current sense device 122) and also a voltage measurement representative of the source voltage $U_{source}$ (e.g., voltage $V_c$ applied to the coil) applied to the coil of the electromagnetic pump 20 (e.g., as sensed or otherwise measured by voltage sense components 124) to detect end of pump stroke. In one or more embodiments, such measurements are also used to provide stroke position information. As shown in FIG. 5, the source voltage may be taken as a measurement across the coil of the electromagnetic pump 20. Further, the current sensing components may be positioned between the coil of the pump 20 and ground to measure the current passing through the coil of the pump 20.

One will recognize that any suitable measurement or sense devices may be utilized to provide coil current information as well as source voltage information to the control electronics 120 for use in accordance with the present invention. The present invention is not limited to any particular design of providing such information to controller 126.

The controller 126 receives both source voltage measurements and current sensed measurements according to the present invention. The controller 126 then operates on such measurements using one or more various algorithms to detect end of pump stroke. According to one or more embodiments, and which shall be described with reference to FIG. 8, a first flux derivative algorithm may be used to detect end of stroke according to the present invention.

Figure 8:
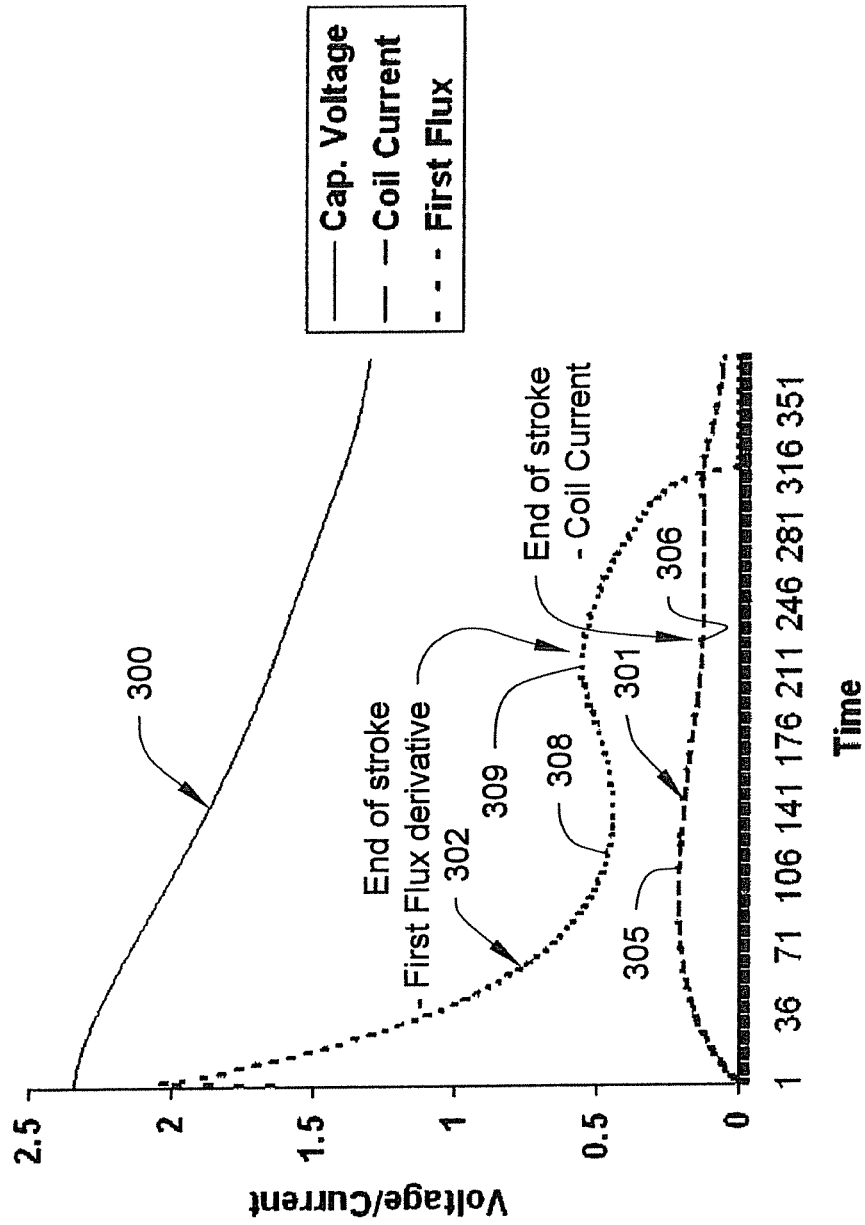
FIG. 8 is a graphical diagram of exemplary voltage characteristics of a power discharge capacitor, current characteristics of a coil operatively connected to the power discharge capacitor, and a calculated first flux derivative waveform according to one embodiment of the present invention.

FIG. 8 shows exemplary waveforms for one exemplary electromagnetic pump. The source voltage or capacitor voltage waveform 300 (i.e., a measured voltage) is shown by line 300. In other words, in this particular exemplary embodiment, the capacitor starts discharging between 2 to 2.5 volts. This capacitor voltage can be sensed at or otherwise obtained by taking one or more measurements over time, and provided to the controller 126.

Also, as shown in FIG. 8, a coil current passing through the coil of the electromagnetic pump is shown by the dashed waveform 301. The coil current waveform 301 may be provided to the controller 126 by the current sense device 122, such as shown in FIG. 5, by sensing the coil current over time. With the coil current and capacitor voltage being provided over time, a first flux derivative waveform may be mathematically calculated according to the following equation:

$$U_{source} - (R_{coil} I_{coil})$$

where $U_{source}$ is the source voltage, $R_{coil}$ is the coil resistance, and $I_{coil}$ is coil current. This particular equation results in a waveform over time that represents the first flux derivative or the change in flux with respect to time or dFlux/dt. As shown in FIG. 8, the first flux derivative waveform 302, calculated as indicated herein, includes a trough 308 generally corresponding to current peak 305 of the current waveform 301, and a peak 309 that is indicative of the end of the pump stroke. As shown in FIG. 8, this particular current waveform 301 does not include a discernible current inflection point at the end of pump stroke in the region 306 of the coil current waveform 301. This is quite unlike the readily apparent current inflection point shown in FIG. 7. In other words, first flux derivative waveform 302 clearly shows a peak 309 corresponding to the end of the pump stroke that can be detected according to the present invention while a coil current inflection may or may not be detectable in region 306 of the coil current waveform 301.

Figure 9:
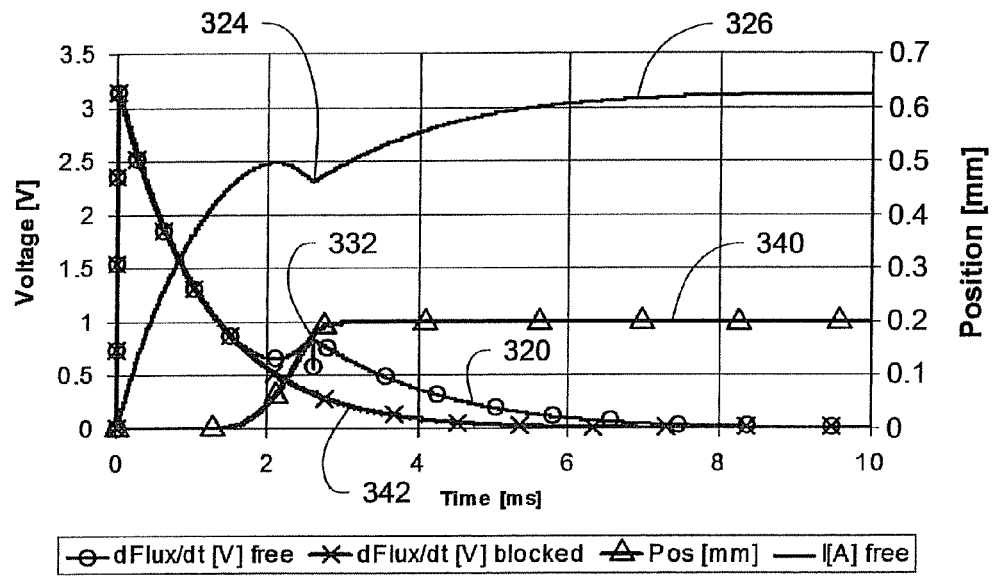
FIG. 9 is a graphical diagram of exemplary current characteristics of a coil connected to a power discharge capacitor, calculated first flux derivative waveforms, and position information according to one or more simulated embodiment of an electromagnetic pump according to the present invention.
Figure 10:
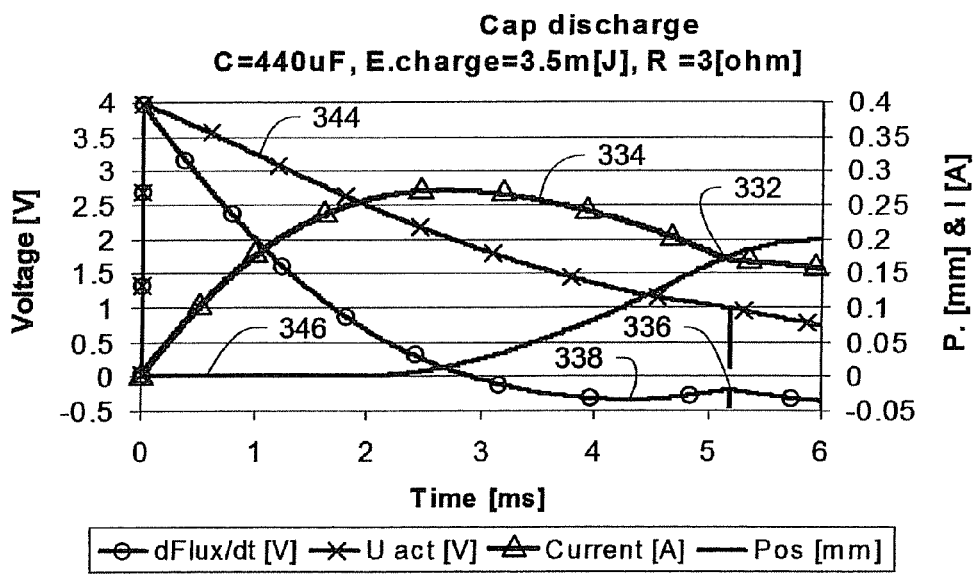
FIG. 10 is a graphical diagram of exemplary voltage characteristics of a power discharge capacitor, current characteristics of a coil connected to the power discharge capacitor, a calculated first flux derivative waveform, and position information according to one or more embodiments of an electromagnetic pump according to the present invention.

FIGS. 9 and 10 show a comparison between two pump stroke illustrations. In FIG. 9, it is illustrated that the first flux derivative waveform 320 for a free piston (i.e., that is allowed to moved) includes a peak point 322 that corresponds to an inflection point 324 of the current waveform 326, both of which (i.e., the peak 322 and inflection point 324) are representative of the end of pump stroke. However, FIG. 10 shows a graph representative of a case where the inflection point of the current waveform 334 is hardly discernible, whereas the peak 336 of the first flux derivative waveform is clearly apparent and easily detectable. The graph of FIG. 9 further includes a position waveform 340 indicative of a position of the actuator of the pump (e.g., a position that stays virtually the same after the end of stroke is reached). Further, a first flux derivative waveform 342 where the piston is blocked (e.g., prevented from moving) as opposed to being in a free state is also shown. When the piston is blocked, no inflection points in either the first flux derivative waveform occur. Further, FIG. 10 includes a source voltage waveform 344, as well as a position waveform 346 (e.g., indicative of the position of the actuator of the pump).

As such, the calculated first flux derivative waveform may be used to detect end of pump stroke for determining the time to de-energize the coil of electromagnetic pump 20. The control electronics 120 for detecting the end of pump stroke based on the first flux derivative waveform may be carried out in various ways. In one or more embodiments, the control electronics 120 calculates the first flux derivative waveform (e.g., waveform 302 of FIG. 8) over time based on the sensed source voltage and sensed coil current. Peak detection would then be used to detect a peak (e.g., peak 309 in FIG. 8) in the first flux derivative waveform as calculated over time which corresponds to the end of a pump stroke.

In one or more embodiments, control electronics 120 may further analyze the waveforms to more successfully perform peak detection. For example, in one or more embodiments, control electronics 120 may perform trough detection to detect a minimum in the first flux derivative waveform (e.g., trough 308 in FIG. 8) prior to performing peak detection to detect a peak (e.g., peak 309 in FIG. 8) in the first flux derivative waveform corresponding to the end of a pump stroke.

In one or more other embodiments, the control electronics may analyze the sensed current (e.g., current waveform 301) in detecting the end of a pump stroke. For example, in such embodiments, the control electronics 120 may perform peak detection with respect to the sensed coil current information to detect a peak in the coil current (e.g., peak 305, as shown in FIG. 8) prior to performing peak detection to detect a peak (e.g., peak 309 in FIG. 8) in the first flux derivative waveform corresponding to the end of a pump stroke. In one or more circumstances, peak detection may be more easily implemented than trough detection. One will recognize that peak detection and trough detection are clearly known to one skilled in the art and may be implemented in any particular suitable manner.

With the end of stroke detected using the first flux derivative waveform, the control electronics 120 may effectively control switch device 128 to stop discharge of capacitor 114 to the electromagnetic pump 20. In other words, upon detection of the end of a pump stroke, the power source 110 may be disconnected from the coil of electromagnetic pump 20.

Yet further, in one or more embodiments, a back EMF voltage may be calculated using the coil current and the source voltage ($U_{source}$). The control electronics 120 calculates the back EMF voltage (e.g., provides a back EMF waveform over time) according to the following equation:

$$U_{emf} = U_{source} - (R_{coil} + R_{source}) \cdot I_{coil} - L_{coil} \cdot \frac{d}{dt}I_{coil}$$

where $U_{emf}$ is the back EMF voltage, $U_{source}$ is the source voltage, $R_{coil}$ is the coil resistance, $R_{source}$ is the source resistance, $I_{coil}$ is coil current, and $L_{coil}$ is coil inductance (e.g., set to a particular inductance value, such as the coil inductance at the beginning of the stroke).

To use the calculated back EMF voltage to provide for detection of an end of a pump stroke, a back EMF limit value is identified corresponding to a completed pump stroke. For example, such a back EMF limit may be determined by repeated trial operation of an electromagnetic pump.

Figure 11:
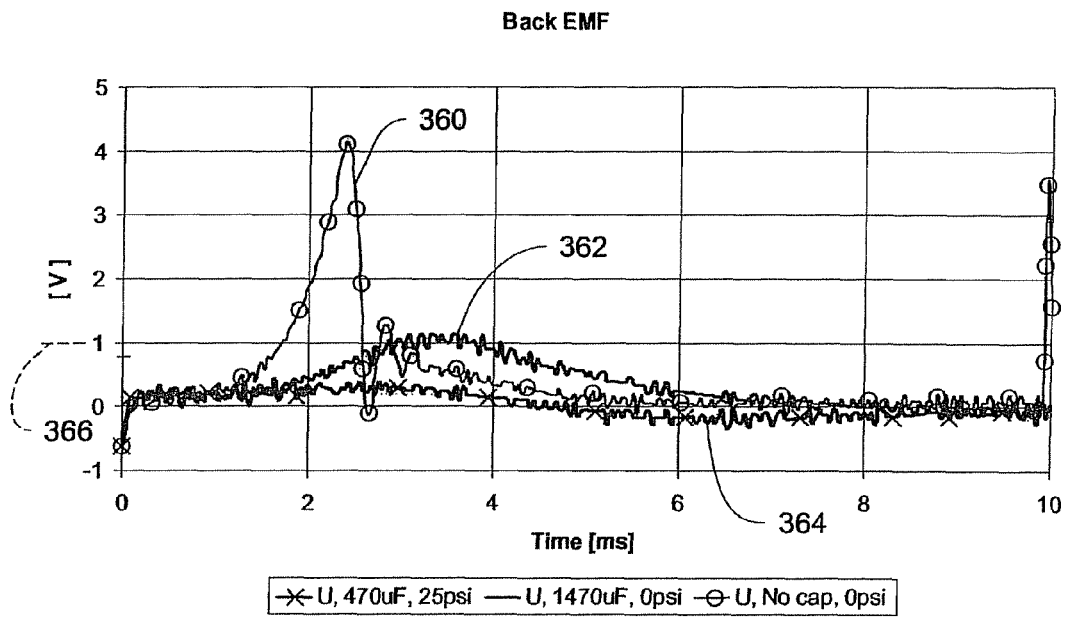
FIG. 11 is a graphical diagram of calculated back EMF voltage for illustrating the use of back EMF in the detection of end of pump stroke according to one or more embodiments of an electromagnetic pump according to the present invention.

FIG. 11 shows a graphical representation of a calculated back EMF voltage based on measurements taken over time for a plurality of illustrative pump embodiments. Calculated back EMF waveforms (i.e., calculated based on current and voltage measurements as opposed to sensed back EMF) are shown where no capacitor is used (waveform 360), a back EMF waveform 362 is provided where a 1470 microfarad capacitor is used, and waveform 364 is provided where a 470 microfarad capacitor is used at 25 psi. As shown in this particular illustrative calculated back EMF diagram, if a threshold limit value 366 of one (1) volt (or something slightly less than one, e.g., 0.75) is set as the back EMF limit when it is know that pump stroke has ended, the calculated waveform 362 when compared to the threshold 366 would indicate an end of pump stroke. The calculated back EMF waveform 360, where an infinite power source is used clearly exceeds this limit as well. However, back EMF waveform 362 (where there is insufficient capacitor size and too large of a back pressure on the piston) does not exceed the limit and end of stroke would not be detected.

It will be recognized that the back EMF algorithm for detection of end of pump stroke may be used alone or it may be used in combination with the first flux derivative algorithm, such as to validate an end of stroke.

Yet further, in one or more embodiments, calculation of inductance from the sensed measurements (e.g., coil current and source voltage) may also be used, for example, at the end of a stroke and/or at the beginning of a stroke, as inductance provides information with respect to the position of the actuator (e.g., relative to the coil). For example, the following inductance algorithm may be used by the control electronics to calculate inductance at the end of the pump stroke with such calculated information being used to determine whether the actuator is in fact at a particular desired position at the end of pump stroke.

Based on the electromagnetic equation of the actuator:

$$L_{coil} = \frac{U_{source} - (R_{coil} + R_{source}) \cdot I_{coil} - \gamma \cdot \omega_{pist}}{\frac{d}{dt}I_{coil}}.$$

where $U_{source}$ is the source voltage, $R_{coil}$ is the coil resistance, $R_{source}$ is the source resistance, $I_{coil}$ is coil current, $L_{coil}$ is coil inductance, $\gamma$ is the electromagnetic coupling factor between the back EMF voltage and pole velocity, and $\omega_{pist}$ is piston velocity.

For a non-moving piston, since $\omega_{pist}$ is zero, it can be assumed that:

$$\gamma \cdot \omega_{pist} = 0$$

Figure 12:
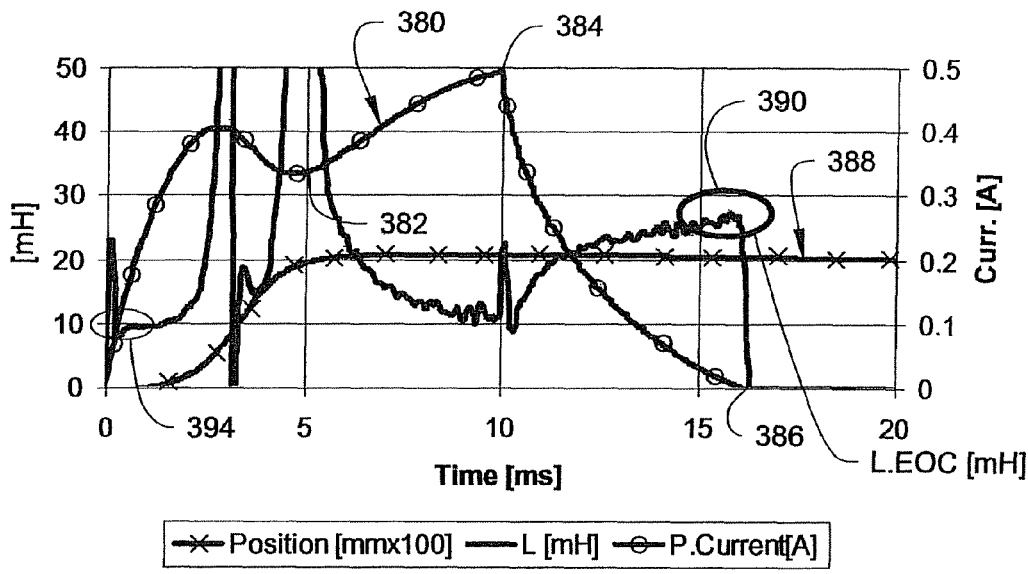
FIG. 12 is a graphical diagram of exemplary inductance waveforms for use in illustrating the determination of position of an actuator of an electromagnetic pump according to one or more embodiments of the present invention.

FIG. 12 shows a graphical diagram of exemplary current, position, and inductance characteristics of one embodiment of a pump, where pump head pressure is zero and no capacitor is used for discharge. As shown in FIG. 12, the current waveform 380 shows an end of pump stroke at point 382 as indicated by the current inflection at this point. When the electrical potential is removed from the coil, the current through the coil begins to fall to zero (i.e., point 386). The actuator position waveform 388 shows that about the time corresponding to the end of stroke (i.e., point 382), the position of the actuator is thereafter substantially maintained.

At the end of the voltage pulse energizing the coil (i.e., point 384), the current falls to zero (i.e., point 386) and so does the actuator force. At this point, the piston starts to move back very slowly due to the beginning of the refill phase of the pump. Since the current value also affects inductance, a point is selected where the inductance can be calculated. Although other points may be selected upon or after detection of end of stroke, one possible selection point is where the current falls to zero since this condition is fulfilled in all external conditions. However, inductance cannot be calculated after the end of current (EOC) has been reached since after this point, the current variation would tend to zero and the division by dI/dt would lead to an indetermination. Therefore, at least in one embodiment, the inductance is windowed (e.g., measurements in a window of time are selected, buffered or otherwise retained) prior to EOC being actually reached. For example, the inductance may be windowed by a window width equal to the EOC time (e.g., time it takes the current to fall to zero after power is removed from the coil at the end of stroke). Further, for example, inductance may be measured over a time period (e.g., before the EOC is reached) and the mean value over the time period (e.g., 2 milliseconds) may be used to remove noise from the calculated inductance.

As such, the inductance EOC ($L_{coil\_EOC}$) is defined as follows:

$$L_{coil\_EOC} = \frac{U_{source} - (R_{coil} + R_{source}) \cdot I_{coil} - \gamma \cdot w_{pist}}{\frac{d}{dt}I_{coil}}$$

In other words, as shown in the graph of FIG. 12, such inductance EOC is calculated, at least in one embodiment, around region 390.

The voltage level applied to energize the pump coil does not affect the relationship between the measured inductance EOC and the position of the actuator, nor does it appear that capacitor size affects this relationship.

A certain inductance EOC will be reached at the end of the stroke and when compared to a previously determined value or range of acceptable values of inductance EOC for a particular pump system (e.g., using a look up table correlating inductance to position of the actuator), it can be determined if the actuator is actually at the desired position at the end of the pump stroke. For example, if a problem with the pump system occurs (e.g., catheter plugged, air bubbles are present, or a piston was cocked) the inductance EOC would not be as expected and a problem could be detected with the pump system. In other words, such information may be used for diagnostic purposes (e.g., determine position of the actuator based on inductance).

Yet further, the inductance may also be measured at the beginning of the pump stroke when the piston is not moving as shown on the graph of FIG. 12 at region 394. A calculation virtually the same as that shown above for inductance at the end of pump stroke is used. For example, the same noise reduction methods, as well as windowing techniques may be used.

Such information at the beginning of the stroke may be used in a similar manner as the information calculated at the end of pump stroke. For example, it can be determined whether the actuator is retracted all the way as it should be at the beginning of a stroke.

All patents and references cited herein are incorporated in their entirety as if each were incorporated separately. This invention has been described with reference to illustrative embodiments and is not meant to be construed in a limiting sense. As described previously, one skilled in the art will recognize that various modifications of the illustrative embodiments, as well as additional embodiments to the invention and combinations of various elements and/or steps herein, will be apparent to persons skilled in the art upon reference to this description. It is therefore contemplated that the patent and claims will cover any such modifications or embodiments that may fall within the scope of the present invention, as defined by the accompanying claims.

What is claimed is:

1. An electromagnetic pump system comprising:
   an electromagnetic pump comprising a coil that can be energized to produce a pump stroke, wherein the electromagnetic pump further comprises an actuator moveable in response to the energization of the coil;
   a direct current power source connected to selectively energize the coil of the electromagnetic pump, wherein the power source applies a source electrical potential to the coil to pass a coil current therethrough;
   a voltage sense device for sensing the source electrical potential applied to the coil;
   a current sense device for sensing the coil current; and
   control electronics to calculate inductance of the coil as a function of sensed coil current and source electrical potential when the actuator is not moving for use in determining position of the actuator, wherein the control electronics calculates $(U_{source}-(R_{coil}+R_{source})*I_{coil})/d/dt\, I_{coil}$ for use in determining position of the actuator, where $U_{source}$ is source electrical potential, $R_{coil}$ is the resistance of the coil, $R_{source}$ is the resistance of the source, and $I_{coil}$ is the coil current.

2. The system of claim 1, wherein the control electronics calculates inductance after detection of end of stroke and prior to end of current in the coil.

3. The system of claim 1, wherein the system is part of an implantable medical device.

4. A method for use in controlling an electromagnetic pump, the electromagnetic pump comprising a coil that can be energized by a power source to produce a pump stroke and an actuator moveable in response to the energization of the coil, wherein the method comprises:
   applying, using a direct current power source, a source electrical potential to the coil to pass a coil current therethrough to provide a pump stroke;
   sensing the source electrical potential applied to the coil;
   sensing the coil current; and
   detecting the end of the pump stroke based on a change in flux over time calculated as a function of sensed coil current and source electrical potential, wherein the change in flux over time is calculated independent of coil inductance $L_{coil}$.

5. The method of claim 4, wherein detecting the end of the pump stroke comprises calculating $U_{source}-(R_{coil}*I_{coil})$ over time corresponding to the change of flux over time, where $U_{source}$ is source electrical potential, $R_{coil}$ is the resistance of the coil, and $I_{coil}$ is the coil current.

6. The method of claim 5, wherein detecting the end of the pump stroke comprises performing peak detection to detect a peak in $U_{source}-(R_{coil}*I_{coil})$ as calculated over time corresponding to the end of a pump stroke.

7. The method of claim 5, wherein detecting the end of the pump stroke comprises performing trough detection to detect a minimum in $U_{source}-(R_{coil}*I_{coil})$ as calculated over time prior to performing peak detection to detect a peak in $U_{source}-(R_{coil}*I_{coil})$ corresponding to the end of a pump stroke.

8. The method of claim 5, wherein detecting the end of the pump stroke comprises performing peak detection to detect a peak in $I_{coil}$ as sensed over time prior to performing peak detection to detect a peak in $U_{source}-(R_{coil}*I_{coil})$ corresponding to the end of a pump stroke.

9. The method of claim 4, wherein selectively applying a source electrical potential to the coil comprises connecting the power source to the coil at the initiation of a pump stroke and disconnecting the power source from the coil upon detection of an end of the pump stroke.

10. The method of claim 4, wherein the method further comprises calculating inductance of the coil as a function of sensed coil current and source electrical potential to verify position of the actuator.

11. The method of claim 10, wherein calculating inductance comprises calculating $(U_{source}-(R_{coil}+R_{source})*I_{coil})/d/dt\, I_{coil}$, where $U_{source}$ is source electrical potential, $R_{coil}$ is the resistance of the coil, $R_{source}$ is the resistance of the source, and $I_{coil}$ is the coil current.

12. The method of claim 10, wherein the method further comprises calculating inductance after detection of end of stroke and prior to end of current in the coil.

13. The method of claim 4, wherein the pump stroke delivers infusion medium.

14. A method for use in controlling an electromagnetic pump, the electromagnetic pump comprising a coil that can be energized by a power source to produce a pump stroke and an actuator moveable in response to the energization of the coil, wherein the method comprises:
   applying, using a direct current power source, a source electrical potential to the coil to pass a coil current therethrough to provide a pump stroke;
   sensing the source electrical potential applied to the coil;
   sensing the coil current; and
   calculating inductance of the coil as a function of sensed coil current and source electrical potential for use in determining position of the actuator, wherein calculating inductance comprises calculating $(U_{source}-(R_{coil}+R_{source})*I_{coil})/d/dt\, I_{coil}$, where $U_{source}$ is source electrical potential, $R_{coil}$ is the resistance of the coil, $R_{source}$ is the resistance of the source, and $I_{coil}$ is the coil current.

15. The method of claim 14, wherein the method further comprises calculating inductance after detection of end of pump stroke and prior to end of current in the coil.

* * * * *